(12) United States Patent
Dyckman

(10) Patent No.: US 6,656,429 B1
(45) Date of Patent: Dec. 2, 2003

(54) STERILIZER VACUUM TEST PACK

(75) Inventor: John D. Dyckman, Commack, NY (US)

(73) Assignee: Propper Manufacturing Co., Inc., Long Island City, NY (US)

( * ) Notice: Subject to any disclaimer, the term of this patent is extended or adjusted under 35 U.S.C. 154(b) by 0 days.

(21) Appl. No.: 09/450,646

(22) Filed: Nov. 19, 1999

(51) Int. Cl.$^7$ ............................................. G01N 21/00
(52) U.S. Cl. ............................. 422/61; 422/58; 436/1
(58) Field of Search .................... 422/58, 61; 436/1

(56) References Cited

U.S. PATENT DOCUMENTS

| | | | |
|---|---|---|---|
| 4,576,795 A | 3/1986 | Bruso | 422/58 |
| 4,579,715 A | 4/1986 | Bruso | 422/58 |
| 4,596,696 A | 6/1986 | Scoville, Jr. | 422/61 |
| 4,636,472 A | 1/1987 | Bruso | 435/287 |
| 4,692,307 A | 9/1987 | Bruso | 422/58 |
| 4,699,765 A | 10/1987 | Hambleton | |
| 4,828,797 A | 5/1989 | Zwarun et al. | 422/55 |
| 4,863,867 A | 9/1989 | Joyce et al. | 435/287 |
| 4,902,478 A | 2/1990 | Hambleton | 422/56 |
| 4,918,003 A | 4/1990 | Macaro et al. | 435/31 |
| 5,435,971 A | 7/1995 | Dyckman | 422/61 |
| 5,824,553 A | * 10/1998 | McCormick et al. | 436/1 |

FOREIGN PATENT DOCUMENTS

| | | |
|---|---|---|
| EP | 0460323 | 12/1991 |
| EP | 0553519 | 8/1993 |
| EP | 0763363 | 3/1997 |

* cited by examiner

*Primary Examiner*—Jill Warden
*Assistant Examiner*—LaToya Cross
(74) *Attorney, Agent, or Firm*—Ostrolenk, Faber, Gerb & Soffen, LLP

(57) ABSTRACT

A test pack for testing the adequacy of air removal in a prevacuum sterilizer. The test pack including a first plurality of planar sheets of substantially porous material disposed to form a stack; a second plurality of planar sheets of substantially porous material disposed to form a stack; an indicator adapted to provide an indication of the removal of air within the test pack and the replacement of the air by sterilizing gas; the indicator being disposed between the first and second pluralities of planar sheets; a tray formed of a gas inhibiting material, the tray having a base coextensive and aligned with an exposed side of one of the first and second pluralities of sheets and four side walls transverse to the base together substantially covering the exposed edges of the first and second pluralities of sheets having the indicator sandwiched between the first and second pluralities of sheets; the tray and the first and second pluralities of sheets with the indicator sheet disposed therebetween defining an assembly, the tray being open on one side opposite the base such that a surface of one of the first and second pluralities of sheets is not covered; and an organizer disposed all about the periphery of the assembly to maintain the sheets and the tray in a predetermined spatial relationship while permitting the passage of sterilizing gas and air to and from the assembly.

29 Claims, 7 Drawing Sheets

STERILIZER VACUUM TEST PACK

BACKGROUND OF THE INVENTION

The present invention relates generally to devices for testing the adequacy of air removal in a sterilization apparatus, and in particular, a prevacuum sterilization apparatus utilized for sterilizing medical equipment. Even more particularly, the present invention relates to a test pack having a steam reactive chemical indicator to determine the efficacy of air removal in a sterilization apparatus. The present invention is particularly useful, although not exclusively useful, for the testing of air removal in prevacuum sterilization equipment used for the steam sterilization of hospital medical equipment.

The sterilization of medical equipment by exposure to sterilization gas such as steam is typically accomplished by using an autoclave. Normally the equipment to be sterilized is placed into the autoclave and a vacuum may or may not be drawn depending on the particular procedure being followed. The sterilization medium, steam, is then introduced into the autoclave to permeate the equipment and sterilize it.

In the gravity displacement steam sterilizer, a sterilizer chamber, with objects to be sterilized within, is subjected to steam for a predetermined period of time. The steam inlet to the camber is typically located in the middle of the rear wall of the chamber. Because steam is lighter than air, it will accordingly rise towards the top of the chamber, displacing the air towards the bottom of the chamber and out the chamber drain. A temperature sensor and a thermostat are provided in the exhaust line to detect when the temperature rises sufficiently, indicating that steam is exiting the chamber, and that, accordingly, air has been completely displaced by the steam.

The above described sterilization apparatus is called a gravity displacement steam sterilizer because gravity and steam under pressure are relied on to cause the lighter steam to displace the heavier air towards the drain in the bottom of the chamber. Because the chamber is constantly under positive pressure, it is impossible for air to enter. The entry of steam under pressure and the operation of the thermostat in the drain ensure total air removal.

In another form of sterilizer, called a prevacuum sterilizer, shown schematically in FIG. 10, the vacuum pump 100 is usually first operated before steam is supplied into the sterilizing chamber 102 to evacuate the air in the chamber. Once air has been partially evacuated, after operation of the pump for a sufficient time, steam is introduced into the chamber via steam inlet 104 until a specified pressure is reached. A series of vacuum pulses followed by introductions of steam are used depending on the model of sterilizer. These steam/vacuum pulses are designed to remove virtually all the air from the chamber and the packs within. After the final vacuum, steam is introduced into the chamber until the correct sterilization temperature/pressure is attained. During the vacuum phase, air reentry is possible because the chamber is under a negative pressure. Air can be drawn into the chamber via leaks in the door gasket or other areas. In these instances, the residual air in the chamber and packs can act as a deterrent to steam penetration into the packs to be sterilized.

According to recommended procedures, steam sterilization equipment in hospitals and other health care facilities needs to be periodically tested to ensure the sterilization procedure is efficacious. In one test, resistant bacterial spores are subjected to the sterilization cycle and subsequently observations are made as to whether they have remained viable. To ensure the sterilization process is adequate, the spores are placed into a specified challenge pack. This pack is designed to challenge penetration by steam as much as or better than the challenge provided by standard hospital packs and packaging. The test is carried out in a normally loaded sterilizer under normal conditions. It is a true test of the sterilizer's ability to sterilize. This test is known as a biological test.

Several procedures have been proposed to test the sterilization efficacy of steam sterilization equipment. Typical of these and perhaps the best known and most widely accepted, is the procedure recommended by the Association for the Advancement of Medical Instrumentation (AAMI) as ANSI/AAMI ST46-1993 ("Good Hospital Practice: Steam Sterilization ad Sterility Assurance"). According to the AAMI recommended practice, 16 freshly laundered all cotton towels are folded by hospital personnel and stacked to construct a challenge test pack approximately 6 inches high. The biological indicator is embedded into the center of this challenge pack. This pack is then subjected to the sterilization cycle as part of a routine sterilization load.

Although apparently efficacious for its intended purpose, the construction of a biological challenge pack according to the AAMI procedure is labor intensive and the resulting pack is relatively bulky.

Applicant's prior U.S. Pat. No. 5,345,971 provides a biological challenge type test pack which obviates the problems inherent in the AAMI procedure by providing a disposable biological challenge pack which has the same performance characteristics as the referenced AAMI towel challenge pack. It is suitable for use as a sterilization test pack for hospital sterilizers.

A different type of test, which employs a different test pack is also recommended for the routine testing of hospital sterilizers. This test is limited to prevacuum sterilizers only. The aim in a prevacuum sterilizer is to remove virtually all air prior to the final introduction of steam for sterilization into the chamber. A test pack known as a Bowie-Dick test pack has been used in such prevacuum tests in the past. In particular, the test pack 112 of FIG. 10 is used to determine the adequacy of the air removal from inside the test pack and replacement of the air by steam. Unlike the biological test, this is not a test of sterilization. It is solely a test of air removal. It is carried out under conditions where the test pack is the only pack in the sterilizer, whereas the biological challenge pack is used in a full load.

In these Bowie-Dick types of test packs, the pack includes a sheet of paper printed with a steam-reactive ink which will change color in the presence of steam under pressure, but will not change color in the presence of air heated to the same degree as steam. The pack is placed into a prevacuum sterilizer, and a cycle is run. The test sheet is removed from the pack and examined to determine if air was removed and replaced by steam. If the air removal has been adequate, the indicator ink will have uniformly changed color throughout the test sheet due to the even presence of steam in the pack and no residual air entrapped in the pack. If the air removal process was in some way defective, air would be trapped in the center of the pack, and its presence would prevent steam from evenly contacting the test sheet and steam reactive ink. In this case, the reactive ink throughout the test sheet would exhibit an uneven color development. Since it is the only pack in the sterilizer, the Bowie-Dick pack provides a sensitive detector of the presence of residual air. If air is not detected by this pack, it can be assumed that air will be adequately removed from packs and will not reenter them during a sterilization run in a fully loaded sterilizer.

In order to assist personnel in determining if color development was correct, and thus air removal was complete, a sample of a correctly exposed test sheet or simulation as well as sheets showing marginal as well as major air entrapment are usually provided for comparison purposes.

An example of a prior art Bowie-Dick test pack is shown in FIG. 9. The figure shows a number of stacked towels about 10–11 inches in height, about twelve inches in length and about 9 inches in width with a Bowie-Dick test sheet or crossed tape disposed at approximately the center of the height dimension. The test sheet has deposited ink or a tape thereon which changes color in the presence of steam. The assembled stack 114 is then wrapped in an air and steam permeable overwrap 116 which is folded about the stack. This arrangement is quite bulky and time consuming to assemble, and clearly does not provide a quick, simple and time-saving vacuum removal testing device. It has substantial differences in construction and use as compared to a biological challenge pack.

The biological test pack as shown in U.S. Pat. No. 5,435,971, although useful as a test of sterilization, is not useful as an air removal test in a prevacuum sterilizer, since it is incapable of providing an evaluation of whether air has been sufficiently evacuated. This is because it is not designed for this purpose, but instead for the purpose of testing sterilization efficacy. It has been shown to be comparable in performance to the AAMI recommended biological challenge pack of 16 towels 6 inches high.

U.S. Pat. Nos. 4,579,715, 4,576,795 and 4,692,307 to Bruso show prevacuum sterilizer test packs. U.S. Pat. No. 4,596,696 to Scoville Jr. shows another form of prevacuum sterilizer test pack. Each of these patents disclose a test pack comprising a chemical indicator which is sandwiched between two pluralities of sheets of porous material. In the Bruso devices, the porous material, both on the top and bottom, is covered by non-porous or impermeable layers. These test packs substantially prevent gas movement through the top and bottom surfaces and only allow gas to flow substantially through the sides of the porous sheets of the test pack. For example, each of the three Bruso vacuum test pack patents show a substantially impermeable top layer 16 (and bottom layer 30) which inhibits gas flow through the top (and bottom). This leads to problems with respect to precluding gas flow to and from the interior through the top surface, thereby emphasizing the flow of gas to and from the interior along the edges and intermediate the porous sheets of paper. This contributes to making the test pack highly sensitive to the degree of tightness with which an overwrap material is applied thereto by affecting the ability of the gas blocked by the gas impermeable layer or layers on the top and bottom to reach the interior.

The devices of the Bruso patents, because of their construction allowing gas to ingress and egress through the sides, have been found to be under-sensitive, i.e., residual air present in the test pack at places other than of the chemical indicator is not sensed, thus leading to false and unreliable indications of air removal.

In the Scoville, Jr. patent, the entire test pack is housed in a box made of a paperboard laminated with a polyester film lamination. This makes the box relatively impermeable to steam. In order to allow steam to permeate into the box and to provide a challenge to steam sterilization, holes or slots are provided in the box to allow air egress and steam ingress.

The device of the Scoville, Jr. reference presents significant barriers to the egress of the air and the entry of the steam. The paperboard box in which the pieces of porous material and chemical indicator are housed is substantially air and gas impermeable due to the lamination. The air can only leave the box, and steam enter the box, primarily through the openings provided in the box as well as through cracks at the ends of the box where the box closure flaps are folded together. The Scoville, Jr. device thus is over-sensitive, i.e., it presents what is believed to be an unnecessary degree of air removal challenge and may provide false indications of lack of air removal when in fact air removal has been accomplished.

All previous test pack designs have been based upon packs of symmetrical construction. Air egress and steam entry are inhibited by areas of relatively gas impermeable layers either at the top and bottom or as a total overwrap. This presents a disadvantage in that if a pack is found to be either under-sensitive or over-sensitive during the manufacturing process, the manufacturer must either add or subtract sheets from the stacks which comprise the top and bottom pluralities of paper, vary the porosity of the papers in the stacks, or adjust the chemistry of the ink used on the sheet. This is a time consuming and difficult process.

The biological test pack of the Dyckman '971 patent provides a first plurality of porous sheets having apertures therein for housing a biological indicator and second and third pluralities of unapertured porous sheets on either side of the first plurality of sheets, the plurality of sheets being housed in a tray formed of gas inhibiting material. The tray is open at the top and the tray with the three pluralities of sheets are enclosed in an overwrap covering material or an organizer box. The covering material or organizer box is substantially air and steam permeable while the tray is substantially impermeable to air and steam. This causes the air to egress and the steam to enter essentially through the open-tray planar top of the test pack. The test pack of the '971 patent is not unduly sensitive to the tightness with which the overwrap material is applied thereto because gas and air movement is not primarily through the sides of the test pack, but instead through the top.

The test pack of the '971 patent, being a sterilization biological test pack, is primarily directed to a gravity displacement type steam sterilization apparatus. It is incapable of evaluating the degree of air removal and replacement of air by sterilizing steam. Nor have test packs of its construction been employed in prevacuum sterilizers for testing adequacy of air removal, as these test packs are not designed for this purpose.

However, there is a need for a test pack which is simple to use, reliable, cost-effective and time-saving and which provides an accurate gauge of the degree of air removal in a prevacuum sterilizer. All of the prior art devices for prevacuum sterilizer air removal testing suffer from various disadvantages, as discussed above, and thus, the industry needs a better test pack for this purpose.

The inventor has discovered, contrary to the accepted techniques for making air removal test packs, that a prevacuum sterilizer test pack can be constructed using a substantially impermeable tray similar to the tray of the biological test pack of the '971 patent, and which gives reliable indications of adequacy of air removal.

The invention employs a non symmetrical assembly in which five of the six planar sides of the assembly are disposed next to a relatively gas impermeable laminated tray. This non symmetrical construction causes air egress and steam entry mainly through the top of the assembly.

SUMMARY OF THE INVENTION

It is an object of the present invention to provide a test pack for determining adequacy of air removal in pre-vacuum gas sterilization equipment.

It is yet still a further object of the present invention to provide a test pack which is useful in prevacuum sterilizers where the sterilizing gas is steam.

Yet still a further object of the present invention is to provide a test pack which is simple, reliable, cost-effective and time-saving to use and which provides good results.

Yet still a further object of the present invention is to provide a test pack for testing the adequacy of air removal in a prevacuum steam sterilizer which is not overly or under-sensitive to the degree of air removal.

Yet still a further object is to provide such an air removal test pack which can be customized to present different degrees of air removal challenge.

The above and other objects of the present invention are achieved by a test pack for testing the adequacy of air removal in a prevacuum sterilizer, comprising a first plurality of planar sheets of substantially porous material disposed to form a stack; a second plurality of planar sheets of substantially porous material disposed to form a stack; an indicator adapted to provide an indication of the removal of air within the test pack and the replacement of the air by a sterilizing gas; the indicator being disposed between said first and second pluralities of planar sheets; a tray formed of a gas inhibiting material, the tray having a base coextensive and aligned with an exposed side of one of said first and second pluralities of sheets and four side walls transverse to said base together substantially covering the exposed edges of said first and second pluralities of sheets having said indicator sandwiched between said first and second pluralities of sheets; the tray and the first and second pluralities of sheets with the indicator disposed therebetween defining an assembly, the tray being open on one side opposite the base such that a surface of one of said first and second pluralities of sheets is not covered; and an organizer disposed all about the periphery of the assembly to maintain the sheets and the tray in a predetermined spatial relationship while permitting the passage of sterilizing gas and air to and from the assembly.

BRIEF DESCRIPTION OF THE DRAWING(S)

The invention will now be described in greater detail in the following detailed description with reference to the drawings in which.

DETAILED DESCRIPTION OF EMBODIMENTS OF THE INVENTION

Figure 1:
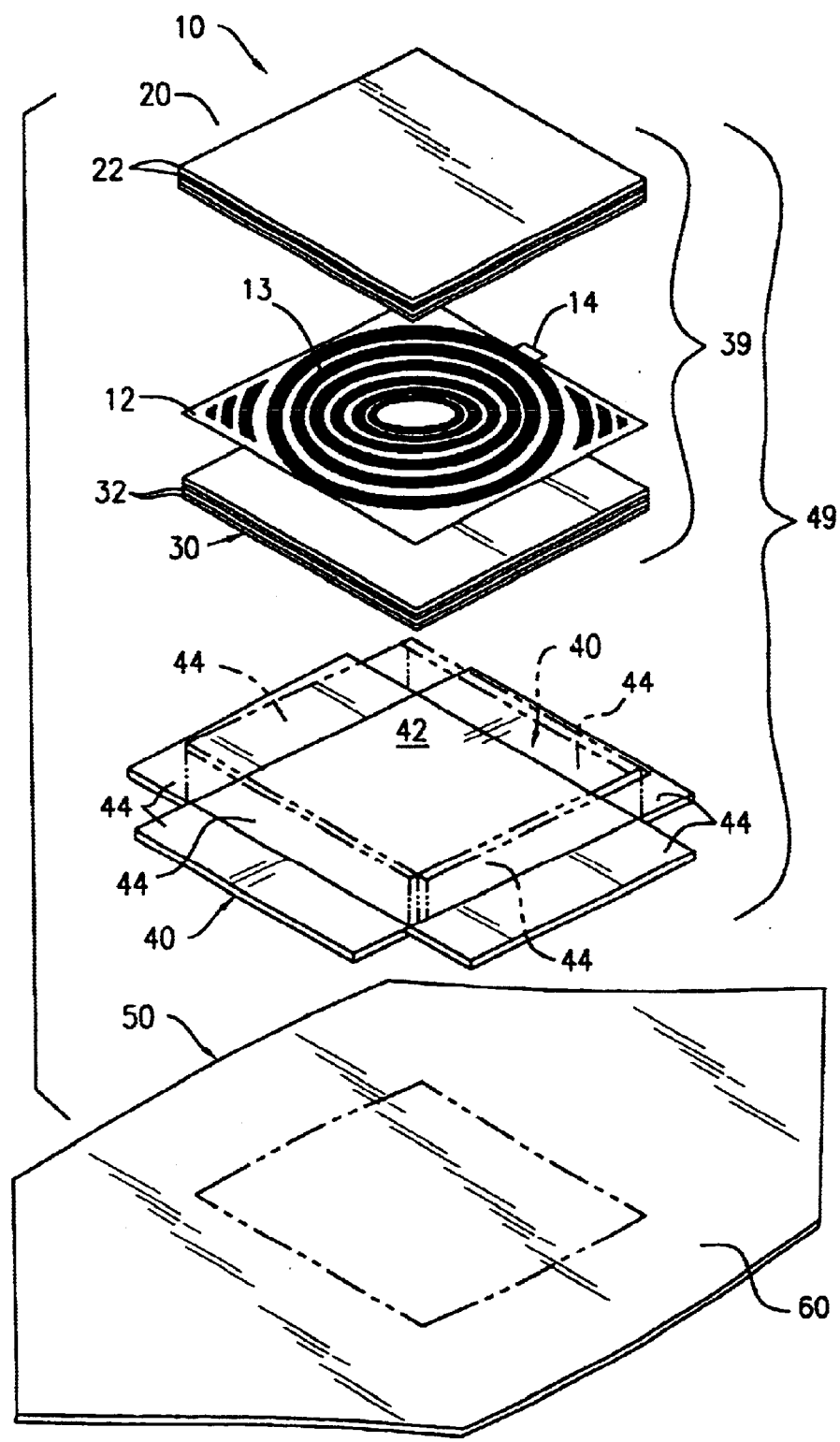
FIG. 1 shows an exploded perspective view of a first embodiment of the test pack according to the present invention.
Figure 2:
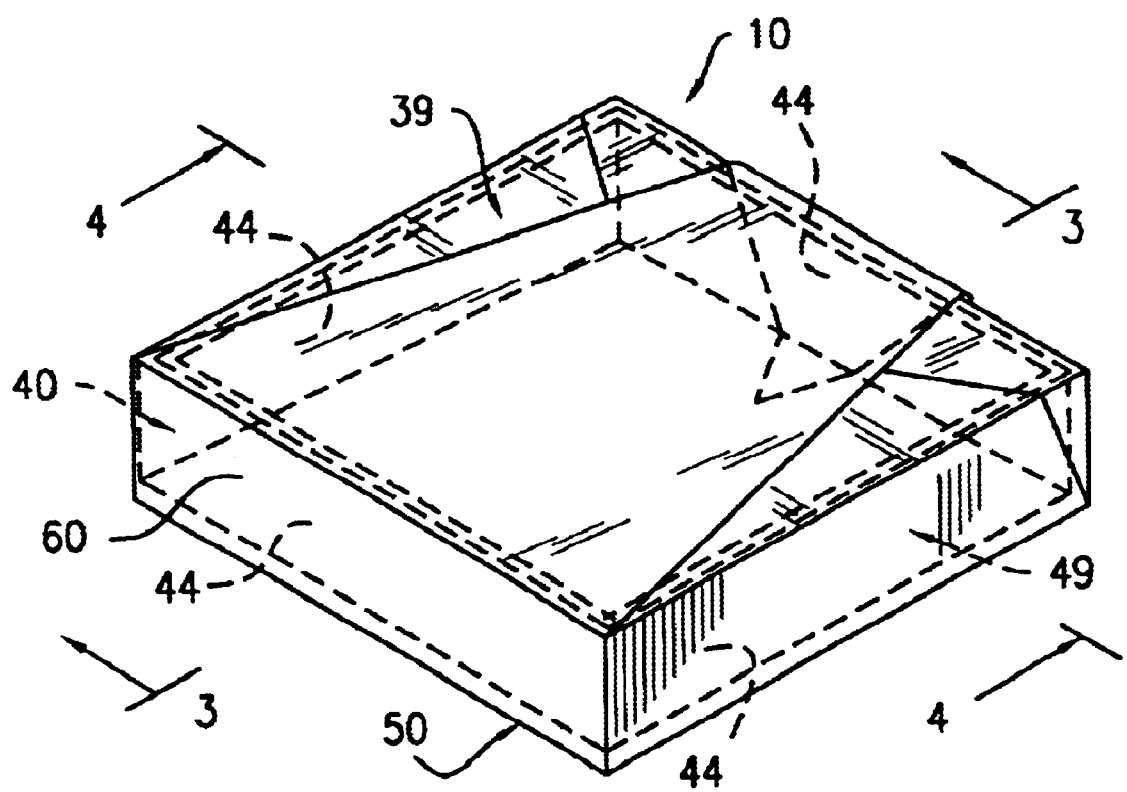
FIG. 2 shows an exploded view of the test pack according to the first embodiment in its assembled state.
Figure 3:
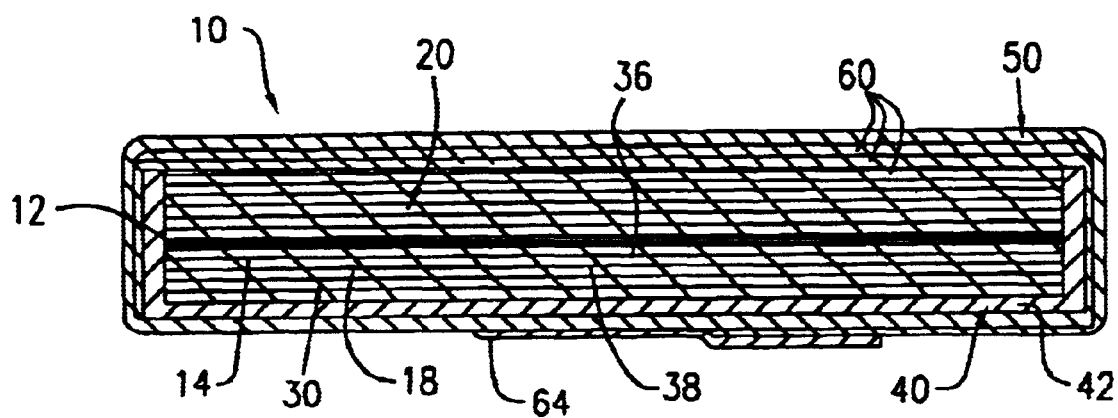
FIG. 3 is a cross-section of the test pack according to the first embodiment taken along lines 3—3 of FIG. 2.
Figure 4:
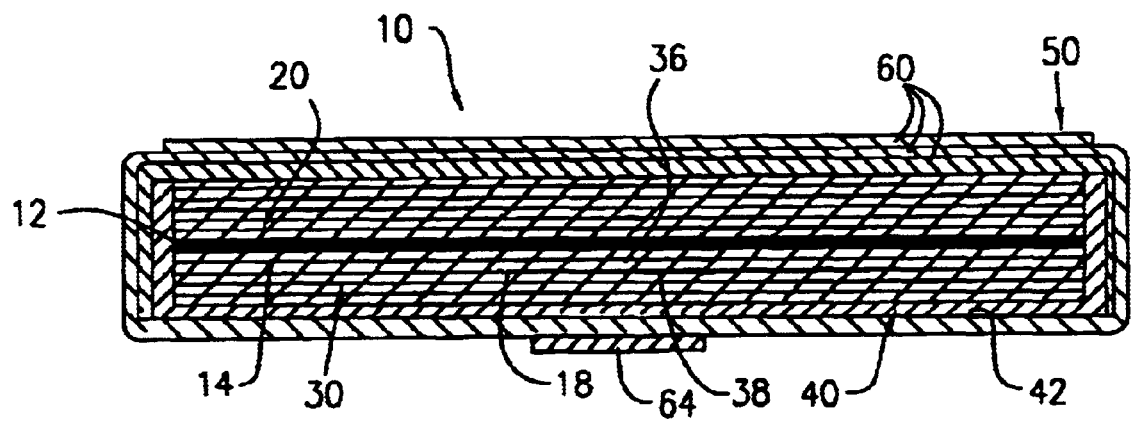
FIG. 4 is a cross-section of the first embodiment taken along lines 4—4 of FIG. 2.

With reference now to the drawings, FIGS. 1–4 show a first embodiment of the test pack according to the present invention which is particularly useful as a test pack for testing the efficacy of air removal in prevacuum type sterilizers.

The test pack, generally designated by reference numeral 10, includes a first plurality 20 of stacked planar sheets 22 of substantially porous material. The sheets 22 are preferably formed of paper which is substantially permeable to both air and steam. The sheets 22 may be approximately 5 by 5 or 5 by 5½ inches in size. Below the stack 20, a chemical indicator test sheet 12, known to those of skill in the art, which is of the same extent as the first plurality of sheets 20, is disposed.

Below the chemical indicator sheet 12, a second plurality 30 of stacked sheets 32 is disposed. These sheets also are made of paper and are preferably substantially air and steam permeable.

The chemical indicator 12 comprises a sheet of paper having printed thereon an ink pattern 13, often in the shape of a bulls eye, as shown. The shape of the indicator pattern is formed by steam sensitive ink which is deposited on the sheet of paper. The ink is specially formulated, as known to those of skill in the art, to change color from a light color to a much darker color, when exposed to steam. If the degree of air removal is inadequate, and thus its replacement by steam is inadequate, the exposure to steam is uneven, and the bulls eye pattern changes color unevenly, thus informing the user that the air removal process has been inadequate. The sheet 12 preferably includes a tab 14 along one side to facilitate location of the chemical indicator sheet.

The pad assembly 39 comprising the first stack 20, the chemical indicator sheet 12 and the second stack 30 are provided into a tray 40, comprising a base 42 having dimensions similar to the pad 39 in cross section and four side walls 44 transverse to the base. The side walls 44 are folded upwardly from the base 42 to form the sidewalls 44. In FIG. 1, the sidewalls 44 are shown prior to folding but are folded upwardly as shown in phantom to be disposed adjacent to the sides of the assembly 39. The tray 40 thus holds the assembly 39 in position.

The tray 40 is formed of a gas inhibiting plastic laminated paperboard. The paperboard is laminated on at least one side with a gas inhibiting material, such as plastic and optionally on both sides. The paperboard is preferably a solid bleached sulfate board having a caliper of about 0.020 inches which is fully laminated on at least one side with the plastic. Any gas inhibiting material such as plastic may be used although polypropylene film, and especially a biaxially oriented polypropylene film, is preferred. The material may be laminated to the paperboard by any conventional means, such as by an acrylic adhesive, capable of withstanding the anticipated moisture and temperature conditions to be experienced by the test pack. The tray base 42 inhibits the passage of gas into the pad assembly 39 through its bottom surface and the tray sidewalls 44 control the passage of gas through the pad 39. While the tray base 42 lies against the bottom of the pad 39, and therefor effectively inhibits the passage of gas through the pad bottom, the tray sidewalls 44 do not abut the pad edges as tightly and thus permit some control of flow of gas through the pad edges.

The height of the side walls 44 are substantially the same as the height of the stacked assembly 39. If the tray side walls extend substantially upwardly from the top of the pad 39, then the pad 39 cannot be sufficiently compressed in the test pack. If the tray sidewalls 44 do not extend upwardly substantially to at least the top of the pad 39, then the sheets of the pad 39 may be overly sensitive to the degree of tightness with which they are held by the overwrap material.

The assembly 49 comprising the assembly 39 and the tray 40 is then assembled into an overwrap 50 which is folded about the assembly 49 and taped together. The entire assembly can then be disposed in the sterilizer for testing the adequacy of the air removal process.

The overwrap sheet 50 in the embodiment shown in FIG. 1 comprises a single sheet 60 of unapertured gas permeable material, commonly known as CSR or sterilization wrap. The highly porous overwrap sheet 60 has essentially no effect on the passage of steam and air into and from the assembly 49. It is permeable to the steam and air. The overwrap sheet 60 is available under the tradename Dextex I from Dexter Corporation or under the tradename Steri-Wrap 1 from Propper Manufacturing Co., Inc. The overwrap sheet 60 is preferably configured as a square of 12×12 to 15×15 inches for a 5×5.5 assembly) and disposed in a conventional hospital wrap format about the assembly 49. The overwrap sheet 60 is fully and tightly wrapped around the assembly 49 so that the passage of steam and air into and from the assembly 49 is essentially and directly through the overwrap sheet 60 rather than through fold openings or the like in the wrapping of the overwrap sheet 60. A short strip of standard one inch wide adhesive autoclave tape 64 (FIGS. 3 and 4) holds the overwrap sheet 60 in the desired overwrapping orientation. This is shown, for example, in FIGS. 2 to 4.

FIGS. 5–8 show a second embodiment of the present invention. In this embodiment, like components are provided with like reference numerals. As in the first embodiment, the assembly 39 comprises first stacked sheets 20, the chemical indicator sheet 12 (shown schematically) and second stacked sheets 30.

Figure 5:
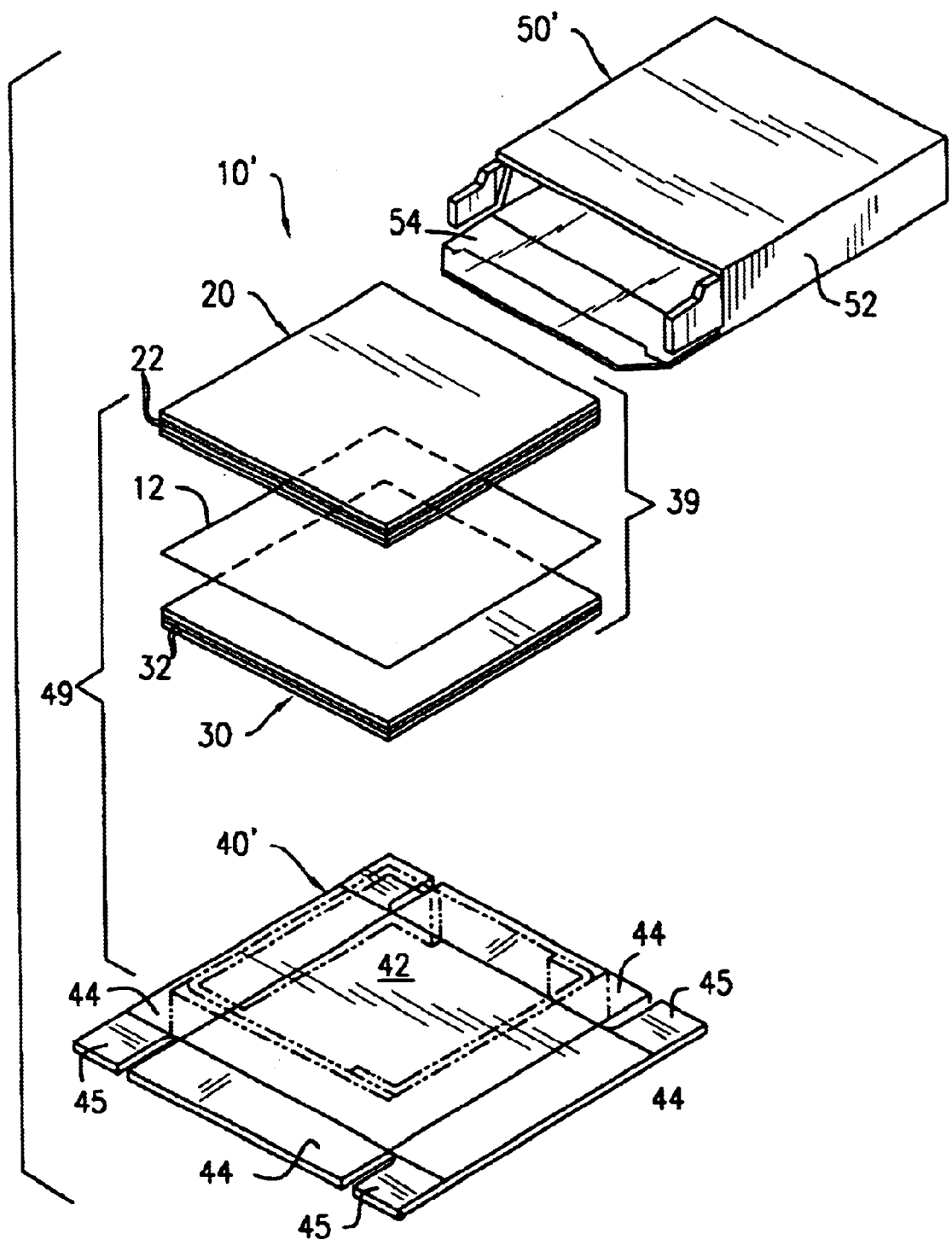
FIG. 5 is an exploded perspective view showing a second embodiment of the test pack according to the present invention.
Figure 6:
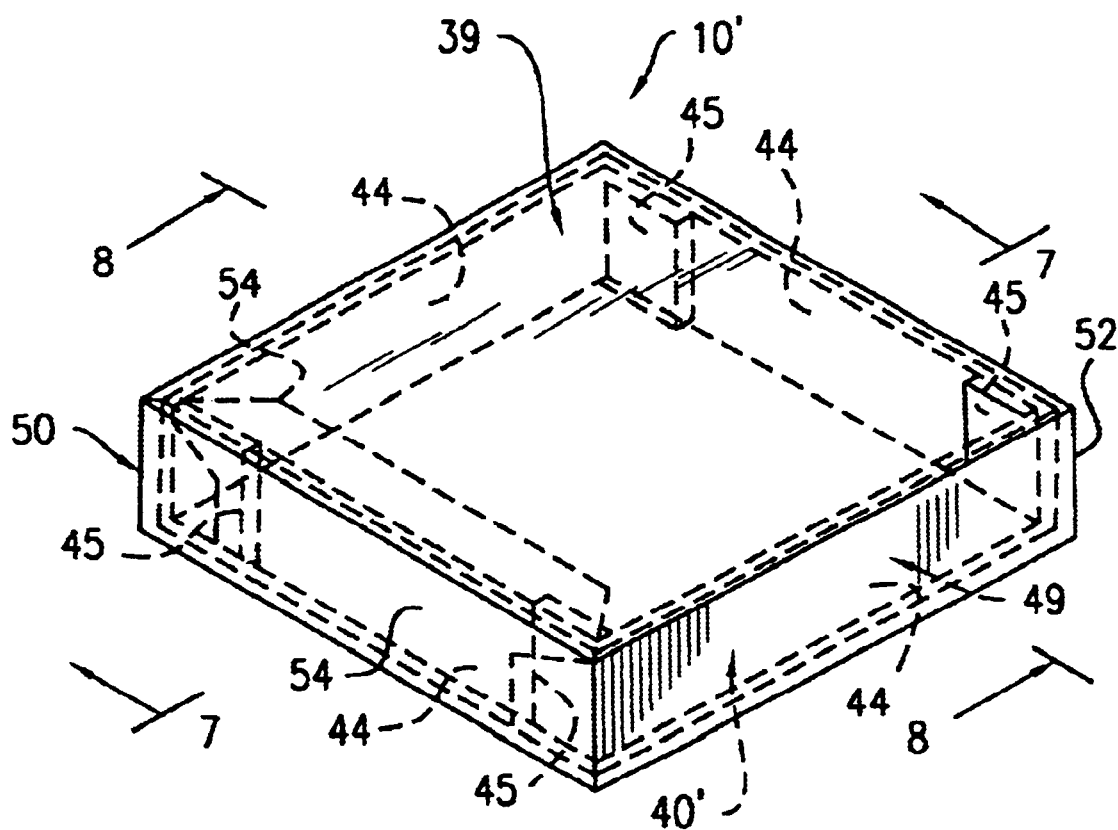
FIG. 6 is a perspective view of the test pack of FIG. 5 shown in its assembled state.
Figure 7:
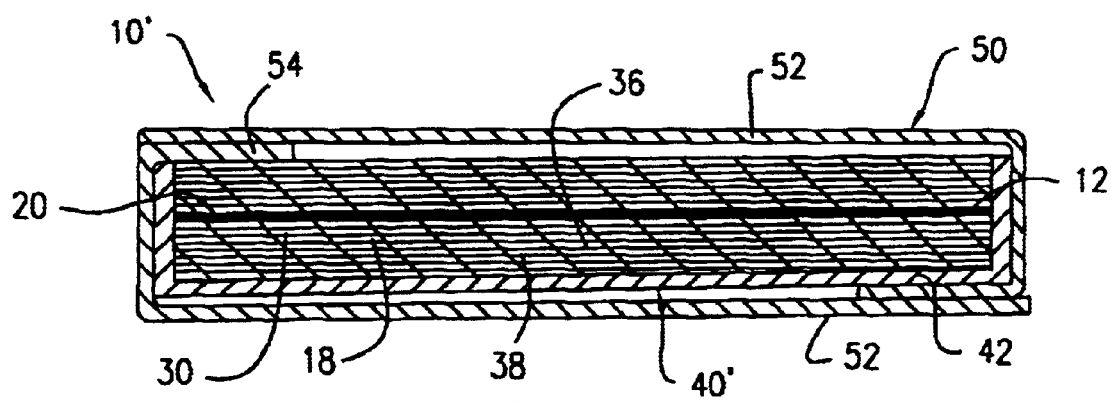
FIG. 7 is a cross-sectional view of the test pack of FIG. 6 taken along lines 7—7 of FIG. 6.
Figure 8:
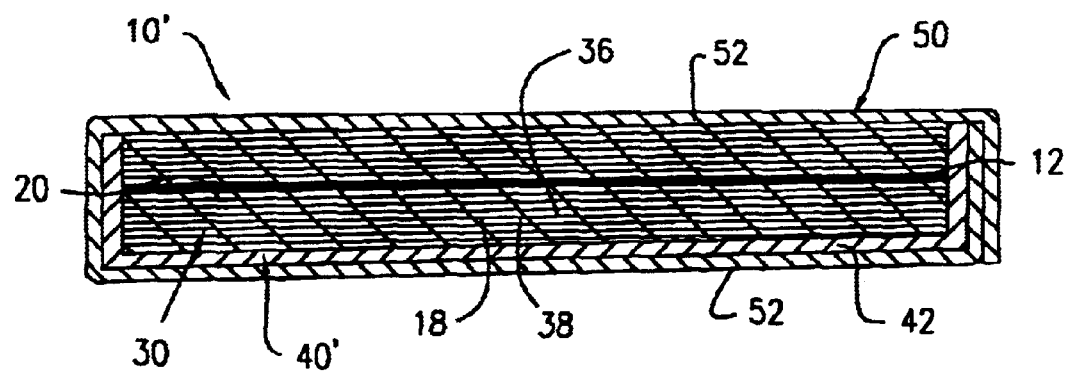
FIG. 8 is a cross-section of the test pack of FIG. 6 taken along line 8—8 of FIG. 6.
Figure 9:
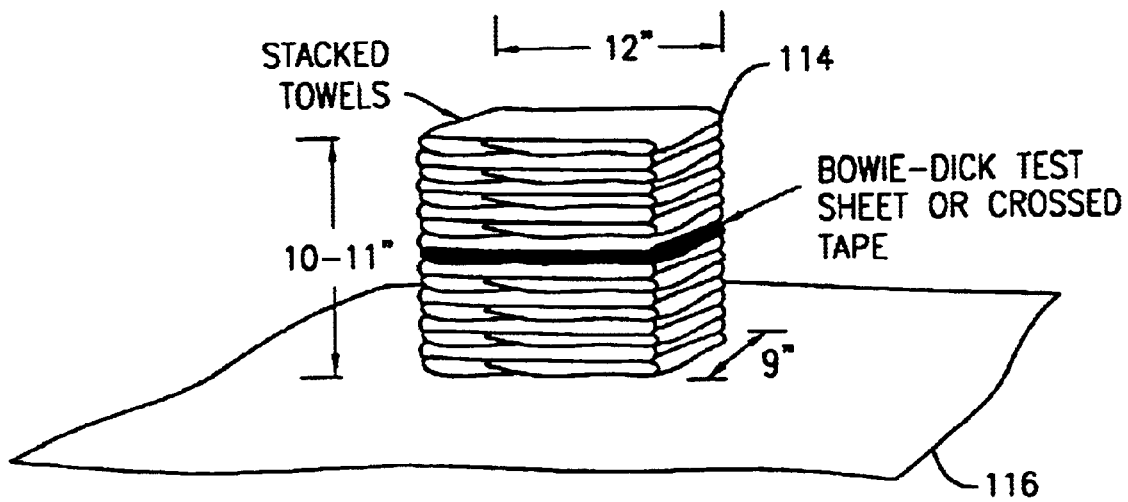
FIG. 9 is a perspective view of the assembly of a prior art Bowie-Dick test pack.
Figure 10:
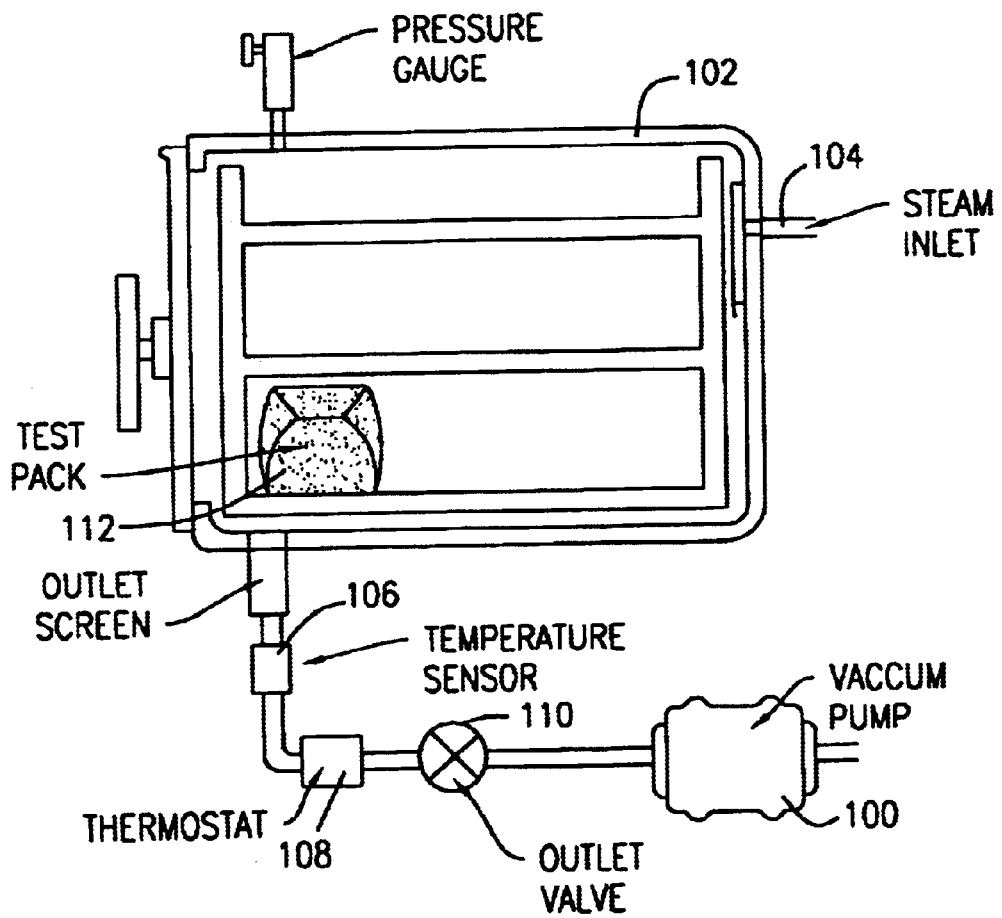
FIG. 10 is a schematic drawing of a prevacuum steam sterilizer.

As shown in FIG. 5, the first plurality of sheets 20, chemical indicator sheet 12 and second plurality of sheets 30 are disposed in tray 40' and inserted inside an organizer box 50' having at least one flap opening and closeable by an end flap 54. The other end may also have a flapped opening.

The flap 54 is moveable relative to the remainder of the box 52 between an open position enabling passage of the assembly 49 therein and therefrom and a closed position maintaining the elements of the assembly 49 therein in a predetermined spatial relationship. The box 52 with the flap 54 in the closed position has an effective gas permeability greater than that of the materials of the pad 39, and of course, the tray 40. The box 52 may be formed of a solid bleached sulfate paperboard, such as 0.020 inch caliper paperboard. Preferably, but not necessarily, the box is provided with pye locks as illustrated at the corners thereof to prevent unintended opening thereof.

The box embodiment 10' of FIG. 5 is generally less sensitive to minor variations in dimensions of the box into which the assembly 49 is inserted than conventional box test packs and thus provides more reliable results. The organizer 50, 50', whether the box 52 or the overwrap sheet 60, has an effective porosity which is at least equal to or greater than that of the pad assembly 39 as a whole. The effective porosity reflects the porosity under the conditions of use, for example, with the organizer 50 in the presence of steam under pressure. The effective porosity, of course, also takes into account not only the actual porosity (that is the ability of the gas to pass directly through the material of the box or overwrap), but also the ability of the gas to pass about the organizer into the pad 39 (for example, between the overlaps of the wrapped overwrap sheet 60 and between the end flaps 54 and the remainder of the box 52 in the box embodiment).

In both embodiments, the first and second stacks are comprised of about 8–14 sheets each and, preferably, 9 sheets each, of heavy porous paper. Preferably, the sheets of the two stacks, and within the two stacks themselves, are of the same composition, but they can be varied in composition to vary the degree of air removal challenge.

In the box embodiment 10' of the present invention, the first and second pluralities of sheets 20 and 30 are optimally comprised of about 9 sheets of heavy porous paper. Thus, the sheets of substantially porous paper for the stack 30 are preferably of the same composition as for the stack 20. In the overwrap embodiment 10, the first and second pluralities 20 and 30 are also each optimally comprised of about 9 sheets of substantially porous paper. Further, the sheets of the first and second pluralities 20, 30 are preferably of the same composition, like in the box embodiment 10. However, the sheets of each stack may be internally varied. Further, the two stacks may have sheets of different porosity.

Each porous paper sheet preferably has an appropriate basis weight of about 214 lbs. (per 3,000 square feet), an appropriate thickness of approximately 0.02 inch per sheet, and a Gurley porosity of approximately 12–35 sec. (using a 20 oz. cylinder). Suitable paper is available from James River Corporation in Richmond, VA. However, other substantially porous papers may be used for the porous sheets 22 and 32. Although the above paper has been found effective, other paper may be used, such as paper having an appropriate basis weight of 178 lbs. (per 3,000 sq. ft.), an approximate thickness of approximately 0.02 inch per sheet, and a Frazier porosity of approximately 1.2–2.0 cu. ft./sq. Ft./min. per sheet.

Frazier porosity is the measure of air permeability of sheet material as measured by the Frazier Differential Pressure Air Permeability Measuring Machine manufactured by Frazier Precision Instrument Company, Inc. of 210 Oakmont Avenue, Gaithersburg, Md. 02760. These measures of porosity are based on the differential pressure principle as measured by manometers. The porosity measure is given in cubic feet of air per square foot per minute at 0.5 inches of water pressure. The Frazier porosities given herein in cubic feet per square foot per minute could be expressed by other standards of measurement. The porosity of stacked porous materials of the type herein used is substantially linear so that, if an individual sheet of material has a Frazier porosity of 90 cu. ft./sq. ft/min., a stack of ten sheets of such material will have a porosity $\frac{1}{10}$ of that of the individual sheet or 9 cu. ft./sq.ft./min.

Another common measure of porosity of sheet material is the Gurley method which provides a measure of the time required for 100 ml. of air to pass through a one square inch area of the specimen material at a given pressure. The Gurley results are comparable to those of ASTM D726-58 (method A).

As will be apparent from the data above, the porosities and permeability specified for the various elements of the test pack of the present invention are specified for the elements at room temperature under standard Gurley and Frazier test conditions. In accordance with known principles, it is believed that the paper elements of the present invention (that is, sheets 22, 32 and the organizer 50) remain relatively constant in porosity over the ranges of temperature and pressure differentials encountered by the test pack during use. On the other hand, in accordance with well known principles, the plastic elements utilized in the tray 40 may exhibit substantial increases in permeability at the elevated temperature and pressure reached during the use cycle. Nonetheless, the tray 40, while exhibiting relatively less permeability at room temperature and a substantially higher permeability at the elevated temperatures, is effective to inhibit the passage of air and steam during the cycle. This is what is meant by reference to the tray as gas inhibiting.

It will be appreciated that only representative sheets 22, 32 of each plurality 20, 30 are illustrated in the drawing. It will further be appreciated that an overwrap embodiment may be used with sheets 22, 32 of the same or different composition just as a box embodiment may be used with sheets 22, 32 of the same or different composition.

The test pack of the present invention is customizable in that the basic sheet elements of the pack may be spatially rearranged (i.e., relocated)—either by the test pack manufacturer or the ultimate test pack user so as to modify the challenge presented by the test pack. Thus, the test pack of the present invention may be adapted for uses which require a more stringent protocol than the standard test, as well as for uses which require a more lenient protocol than the standard test. As long as the same number of total sheets (total height) are used to form a pad 39, the pad 39 is combinable with a tray 40, 40' to form an assembly 49 which can be employed with an organizer 50, 50' regardless of whether the organizer 50, 50' is an overwrap 60 or box 52. In the case of the overwrap 60, the tray sidewalls 44 will still ensure an appropriate tightness of the overwrap about the assembly 40, and, in the case of the box 52, the assembly 49 will still fit therewithin.

Thus, as one or more of the sheets 22 of the first plurality 20 are removed therefrom and added to the sheets 32 of the second plurality 30, the chemical indicator 12 will move upwardly in the pad 39 and assembly 49, thus increasing the ease of air removal and exposure of the indicator 12 to the steam. This occurs because the porous sheets 22 of the diminished first plurality 20 constitute less of an impediment to the passage of air and steam than the tray base 42. The greater the number of sheets 22 relocated into pad 30, the less the challenge of the thus diminished first plurality 20. On the other hand, as one or more of the sheets 32 of the second plurality 30 are removed therefrom and added to the sheets 22 of the first plurality 20, the chemical indicator 12 will move downwardly, further from the top of the pad 39 or assembly 49 and closer to the tray base 42. The greater the number of sheets 32 relocated to the thus enlarged first plurality 20, the thinner the second plurality 30 and the greater the challenge provided as the chemical indicator 12 is closer to the less permeable tray base.

The ability to customize the pack is made possible by the unique asymmetrical pack construction design. In a like manner, the manufacturer or user can overcome variations in properties of the components used to prepare the pack. If the components are found by testing to present either too great or too little of a challenge, the position of the test sheet in the pack can be varied to result in a pack of standard performance without changing the number or properties of the pack components.

Accordingly, one can easily customize the test pack of the present invention from the standard construction to a customized construction simply by relocating porous sheets 22, 32 as necessary to modify in the desired direction the spacing between the chemical indicator 12 and the tray base 42. Accordingly, the test pack of the present invention is customizable either by the manufacturer, or, when it is provided with a removable organizer (whether an overwrap or a box) as shown, in order to enable access to the pad 39, by the user. The customization is made possible by the first and second pluralities 20, 30 being codependently variable by the user (i.e., one or more of the sheets being removed from one plurality and added to the other plurality) so long as the total of the first and second pluralities 20, 30 remains a constant (i.e., so that the combined number of sheets in the first and second pluralities, and thus the combined height thereof, is unchanged).

The present invention thus provides a test pack which simulates the Bowie-Dick vacuum removal test pack and is small, compact, easily handled by hospital personnel, convenient to use, standardized, cost effective, time-saving and easily manufactured. It is easily altered to change the placement of the air removal indicator sheet as desired. The test pack is not overly sensitive to the tightness of a wrapping or box about the pad and employs a gas-inhibiting tray to inhibit the passage of gas into and out of the bottom of the test pack and to control the passage of gas into and out of the edges of the test pack.

Although the present invention has been described in relation to particular embodiments thereof, many other variations and modifications and other uses will become apparent to those skilled in the art. Therefore, the present invention should be limited not by the specific disclosure herein, but only by the appended claims.

What is claimed is:

1. A test pack for testing the adequacy of air removal in a prevacuum sterilizer, the test pack providing equivalence to a standard Bowie-Dick towel test pack, the test pack comprising:

a first plurality of planar sheets of substantially porous material disposed to form a stack;

a second plurality of planar sheets of substantially porous material disposed to form a stack;

an indicator adapted to provide an indication of the removal of air within the test pack and the replacement of the air by a sterilizing gas;

the indicator being disposed between said first and second pluralities of planar sheets;

the indicator comprising a sheet of material having a chemical indicator thereon which changes color in the presence of sterilizing gas;

a tray formed of a gas inhibiting material, the tray having a base coextensive and aligned with an exposed side of one of said first and second pluralities of sheets and four side walls transverse to said base together substantially covering the exposed edges of said first and second pluralities of sheets having said indicator sandwiched between said first and second pluralities of sheets; the tray and the first and second pluralities of sheets with the indicator disposed therebetween defining an assembly, the tray being open on one side opposite the base such that a surface of one of said first and second pluralities of sheets is not covered; and an organizer disposed all about the periphery of the assembly to maintain the sheets and the tray in a predetermined spatial relationship while permitting the passage of sterilizing gas and air to and from the assembly, further wherein said first and second pluralities of sheets comprise a total number of sheets of 16 to 28 sheets of paper having a basis weight of about 214 lbs, a caliper of about 0.02 inch and a Gurley porosity of about 12–35 secs (20 oz cylinder).

2. The test pack of claim 1, wherein the sterilizing gas is steam.

3. The test pack of claim 1, wherein the material of the indicator sheet comprises paper.

4. The test pack of claim 1, wherein said organizer is a sheet of folded porous material for wrapping about said assembly.

5. The test pack of claim 1 wherein said organizer is a box having an integrally hinged flap on one end moveable between an open position enabling passage thereinto and therefrom of said assembly and a closed position maintaining the elements of the assembly therein in the predetermined spatial disposition, the box with said flap in said closed position having an effective porosity greater than that of said assembly.

6. The test pack of claim 1, wherein the sheets of said first and second pluralities are of the same composition.

7. The test pack of claim 5, wherein said box is formed of solid bleached sulfate paperboard.

8. The test pack of claim 7, wherein said paperboard has a caliper of about 0.02 inch.

9. The test pack of claim 5, wherein said box has pyelocks at the corners thereof.

10. The test pack of claim 1 wherein said organizer is an overwrap sheet of paper having a substantial porosity greater than that of said assembly.

11. The test pack of claim 1, wherein the first plurality and the second plurality comprise about 8–14 sheets of paper having a basis weight of about 214 lbs, a caliper of about 0.02 inch and a Gurley porosity of about 12–35 secs (20 oz cylinder).

12. The test pack of claim 10, wherein the overwrap sheet is a crepe non-woven sterilization wrap sheet.

13. The test pack of claim 1, wherein said tray is a paperboard laminated with gas inhibiting material.

14. The test pack of claim 13, wherein the tray is paperboard laminated on at least one side with gas inhibiting plastic.

15. The test pack of claim 13, wherein the paperboard of said tray is solid bleach sulfate board.

16. The test pack of claim 14, wherein the plastic is polypropylene film.

17. The test pack of claim 1, wherein the tray is solid bleached sulfate paper board having a caliper of about 0.020 inch fully laminated on one side by an acrylic adhesive with a biaxially oriented polypropylene film about 0.0014 inch thick.

18. The test pack of claim 1, wherein the base and each of the side walls of the tray are substantially planar.

19. The test pack of claim 1, wherein the sidewalls do not overlap each other.

20. The test pack of claim 1, wherein the sidewalls overlap each other.

21. The test pack of claim 1, wherein the substantially porous material comprises paper.

22. The test pack of claim 1, wherein the number of sheets in each of the first and second pluralities can be varied to customize the test pack.

23. The test pack of claim 1, wherein the porosity of the sheets in each of the first and second pluralities can be varied within each plurality or between the pluralities.

24. A method for testing the adequacy of air removal in a prevacuum sterilizer using a testpack, the testpack providing equivalence to a standard Bowie-Dick towel test pack, and wherein the test pack comprises:

a first plurality of planar sheets of substantially porous material disposed to form a stack;

a second plurality of planar sheets of substantially porous material disposed to form a stack;

an indicator adapted to provide an indication of the removal of air within the test pack and the replacement of the air by sterilizing gas;

the indicator comprising a sheet of material having a chemical indicator thereon which changes color in the presence of sterilizing gas;

the indicator being disposed between said first and second pluralities of planar sheets;

a tray formed of a gas inhibiting material, the tray having a base coextensive and aligned with an exposed side of one of said first and second pluralities of sheets and four side walls transverse to said base together substantially covering the exposed edges of said first and second pluralities of sheets having said indicator sandwiched between said first and second pluralities of sheets; the tray and the first and second pluralities of sheets with the indicator disposed therebetween defining an assembly, the tray being open on one side opposite the base such that a surface of one of said first and second pluralities of sheets is not covered; and an organizer disposed all about the periphery of the assembly to maintain the sheets and the tray in a predetermined spatial relationship while permitting the passage of sterilizing gas and air to and from the assembly;

the method comprising the step of varying the height of each of the first and second pluralities while maintaining the combined height of the first and second pluralities constant, further wherein said first and second pluralities of sheets comprise a total number of sheets of 16 to 28 sheets of paper having a basis weight of about 214 lbs, a caliper of about 0.02 inch and a Gurley porosity of about 12–35 secs (20 oz cylinder).

25. The method of claim 23, wherein the number of total sheets in the first and second pluralities remains a constant. paper.

26. The method of claim 24, wherein the height of each of the first and second pluralities is varied by changing the number of sheets in each of the first and second pluralities.

27. The method of claim 26, wherein the heights of the first and second pluralities are varied by moving at least one sheet from one of the first and second pluralities to the other of the first and second pluralities.

28. A test pack for testing the adequacy of air removal in a pre-vacuum sterilizer, the test pack providing equivalence to a standard Bowie-Dick towel test pack, the test pack comprising:

a first plurality of planar sheets of substantially porous material disposed to form a stack;

a second plurality of planar sheets of substantially porous material disposed to form a stack;

an indicator adapted to provide an indication of the removal of air within the test pack and the replacement of the air by a sterilizing gas;

the indicator being disposed between said first and second pluralities of planar sheets;

the indicator comprising a sheet of material having a chemical indicator thereon which changes color in the presence of sterilizing gas; the indicator sheet of material being directly disposed between the first and second pluralities of sheets without any sheets of material being disposed about edges of said indicator sheet of material;

a tray formed of a gas inhibiting material, the tray having a base coextensive and aligned with an exposed side of one of said first and second pluralities of sheets and four side walls transverse to said base together substantially covering the exposed edges of said first and second pluralities of sheets having said indicator sandwiched between said first and second pluralities of sheets; the tray and the first and second pluralities of sheets with the indicator disposed therebetween defining an assembly, the tray being open on one side opposite the base such that a surface of one of said first and second pluralities of sheets is not covered; and an organizer disposed all about the periphery of the assembly to maintain the sheets and the tray in a predetermined spatial relationship while permitting the passage of sterilizing gas and air to and from the assembly, further wherein said first and second pluralities of sheets comprise a total number of sheets of 16 to 28 sheets of paper having a basis weight of about 214 lbs, a caliper of about 0.02 inch and a Gurley porosity of about 12–35 secs (20 oz cylinder).

29. A test pack for testing the adequacy of air removal in a prevacuum sterilizer, the test pack providing equivalence to a standard Bowie-Dick towel test pack, the test pack comprising:

a first plurality of planar sheets of substantially porous material disposed to form a stack;

a second plurality of planar sheets of substantially porous material disposed to form a stack;

an indicator adapted to provide an indication of the removal of air within the test pack and the replacement of the air by a sterilizing gas;

the indicator being disposed between said first and second pluralities of planar sheets;

the indicator comprising a sheet of material having a chemical indicator thereon which changes color in the presence of sterilizing gas; there being no sheets surrounding the indicator along edges of the indicator so that the indicator is not disposed in a cavity formed in planar sheets;

a tray formed of a gas inhibiting material, the tray having a base coextensive and aligned with an exposed side of one of said first and second pluralities of sheets and four side walls transverse to said base together substantially covering the exposed edges of said first and second pluralities of sheets having said indicator sandwiched between said first and second pluralities of sheets; the tray and the first and second pluralities of sheets with the indicator disposed therebetween defining an assembly, the tray being open on one side opposite the base such that a surface of one of said first and second pluralities of sheets is not covered; and an organizer disposed all about the periphery of the assembly to maintain the sheets and the tray in a predetermined spatial relationship while permitting the passage of sterilizing gas and air to and from the assembly, further wherein said first and second pluralities of sheets comprise a total number of sheets of 16 to 28 sheets of paper having a basis weight of about 214 lbs, a caliper of about 0.02 inch and a Gurley porosity of about 12–35 secs (20 oz cylinder).

* * * * *